United States Patent
Thompson et al.

(10) Patent No.: US 10,470,724 B2
(45) Date of Patent: Nov. 12, 2019

(54) LASER AND ACCELEROMETER GUIDED MEDICAL DEVICE

(71) Applicant: PRECISIONRAD LLC, Scottsdale, AZ (US)

(72) Inventors: Colin Michael Thompson, Scottsdale, AZ (US); Karanjot Singh Sundlass, Green Bay, WI (US)

(73) Assignee: PRECISIONRAD LLC, Scottsdale, AZ (US)

( * ) Notice: Subject to any disclaimer, the term of this patent is extended or adjusted under 35 U.S.C. 154(b) by 693 days.

(21) Appl. No.: 15/097,054

(22) Filed: Apr. 12, 2016

(65) Prior Publication Data

US 2016/0296179 A1    Oct. 13, 2016

Related U.S. Application Data

(60) Provisional application No. 62/146,682, filed on Apr. 13, 2015.

(51) Int. Cl.
*A61B 6/08* (2006.01)
*A61B 34/20* (2016.01)

(52) U.S. Cl.
CPC ............... *A61B 6/08* (2013.01); *A61B 34/20* (2016.02); *A61B 2562/0219* (2013.01)

(58) Field of Classification Search
None
See application file for complete search history.

(56) References Cited

U.S. PATENT DOCUMENTS

| | | | |
|---|---|---|---|
| 6,611,141 B1 | 8/2003 | Schulz et al. | |
| 9,681,823 B2 * | 6/2017 | Messerly | A61B 5/042 |
| 9,814,390 B2 * | 11/2017 | Piron | A61B 90/39 |
| 2012/0089014 A1 * | 4/2012 | Sabczynski | A61B 1/05 |
| | | | 600/424 |
| 2012/0143029 A1 * | 6/2012 | Silverstein | A61B 5/042 |
| | | | 600/374 |
| 2013/0064427 A1 | 3/2013 | Picard et al. | |
| 2013/0066232 A1 | 3/2013 | Schoepp | |
| 2014/0088410 A1 | 3/2014 | Wu | |
| 2014/0107472 A1 | 4/2014 | Roeder et al. | |
| 2014/0135616 A1 | 5/2014 | Stein et al. | |
| 2014/0180074 A1 | 6/2014 | Green et al. | |

FOREIGN PATENT DOCUMENTS

DE          4225112 C1    12/1993

* cited by examiner

*Primary Examiner* — Ronald Laneau
(74) *Attorney, Agent, or Firm* — Jennings, Strouss and Salm; Michael K. Kelly; Daniel R. Pote

(57) ABSTRACT

A positioning device for use with a medical device to assist a user in maintaining the medical device in a desired 3-dimensional orientation, having an anchor for releasably attaching the medical device to the positioning device; a laser for generating an indication of orientation on a surface; an accelerometer for providing an indication of orientation relative to gravity; and a display for providing an indication of said orientation to the user to inform the user to adjust a position of the device relative to the desired position.

17 Claims, 10 Drawing Sheets

LASER AND ACCELEROMETER GUIDED MEDICAL DEVICE

CROSS-REFERENCE TO RELATED APPLICATIONS

The present application claims the benefit of U.S. Provisional Patent Application No. 62/146,682 filed Apr. 13, 2015, the relevant contents of which are incorporated herein by reference.

FIELD OF INVENTION

The present application is generally related to a trajectory guidance device that is fitted to medical devices to aid in advancement of the medical device along a predetermined course for treatment.

BACKGROUND OF THE INVENTION

Numerous medical devices require fine motor skills to effectively and safely provide some form of treatment. A common example would be a medical provider performing a procedure in which a medical instrument is placed into a precise location in the body under imaging guidance. While experience aids medical providers in knowing the appropriate location and manipulations needed to perform the procedure, mechanisms to aid the placement of a device results in greater accuracy, consistency, patient safety, patient comfort, reduced radiation exposure, and shorter duration with regard to procedures.

The majority of computed tomographic (CT) guided procedures involve placing a medical instrument into a target lesion. Example procedures include injections, biopsies, ablations, catheter placement, and fiducial placements. In performing these procedures, in most instances a CT scan is initially performed which allows the operator to evaluate the target of the medical device, and plan a course from the entry point of the device into the patient. Once the target and entry point are determined and, after making sure the course does not transgress a critical structure, the angle of approach can be determined with respect to the orientation of the CT scanner by software and displayed on the CT images on the displays used to control the scanner.

Once the trajectory determined by the target and entry point, and the angle of that line in respect to the CT scanner have been determined, the operator advances the medical device along that course, intermittently rescanning the area to determine the actual position of the medical device and its relation to the intended course, and adjusting as necessary. CT scanners will usually have a laser line that projects from the scanner in the transaxial plane onto the patient to aid in localizing the entry point. However, re-scanning during the procedure is necessary to ensure proper positioning of the device, and any alterations from the planned course require re-positioning of the device and thus result in additional movement of the medical device along, or outside of the pre-determined path. This additional movement, and rescanning to ensure proper positioning of the device increases radiation exposure to the patient, prolongs procedure time, can cause additional trauma to organs within or near the intended trajectory, and may increase pain experienced by the patient.

Many medical device guidance systems have been developed to aid in positioning and movement of the medical instrument. A major limitation with some of these medical device guidance systems is that such systems constrain the motion of the medical device with respect to a patient, bench, CT scanner, room, or some other fixed reference. For example, US 20130066232 discloses a device for trajectory guidance of a needle-like medical instrument through the use of an accelerometer and a line generating laser which is aligned with the laser line of the CT scanner. A needle-like medical instrument is inserted through a rotatable guide sleeve which is locked into a desired orientation based on an initial diagnostic and planning CT scan. The guide sleeve is attached to a base which is constrained with respect to the room or CT scanner. The guide sleeve constrains the trajectory of the needle like medical instrument after the desired orientation is determined. Simple intra-procedural adjustments to the trajectory of the needle-like instrument which can be a common occurrence due to patient motion or when targeting organs subject to respiratory motion, for example, may be extremely cumbersome with this device. In addition, once a needle-like medical instrument is inserted into a patient and is constrained in this manner, any type of patient motion, for example something as common as a cough, may cause significant organ injury such as a major laceration of the organ in which the instrument has been inserted.

Other devices determine orientation by using some combination of accelerometers, gyrometers, magnetometers, optical cameras, GPS, and radiofrequency signaling all with some limitations. For example, US Publication No.'s 20140135616, 20140107471, 20140180074, 20130064427, 20140088410, U.S. Pat. No. 6,611,141, and DE4225112 all disclose devices for medical instrument guidance using some combination of the aforementioned technologies. Accelerometers only measure orientation with respect to gravity limiting their ability to determine 3-dimensional orientation independently. Accuracy of magnetometers is limited in the presence of electromagnetic interference such as from a CT scanner. Gyrometers are prone to rapid signal drift requiring reorientation from a magnetometer or an external reference. Optical cameras determine position of the medical devices relative to fixed references or markers which constrain the device to be within the field of view of the camera and require additional hardware and software. GPS and radiofrequency signaling also require additional hardware and software for sending, receiving, and processing the signals.

In comparison to the prior art devices, the present device provides an effective, simple to use, fast, and inexpensive means of determining 3-dimensional orientation of a medical instrument for the purpose of guidance during a medical procedure. The present device combines a CT scan with a secondary laser and guidance system that allows completely unconstrained movement of a medical instrument, contains all of the required hardware and software in a compact lightweight design, and is compatible with nearly all needle-like medical instruments commonly used during CT-guided procedures.

SUMMARY OF THE INVENTION

In accordance with these and other objects, a first embodiment of the present disclosure is related to a guidance apparatus used in conjunction with a CT scan comprising an accelerometer, a line generating laser, a microcontroller, a display, a battery, a housing, and an attachment mechanism to secure a medical device to the apparatus.

A further embodiment is related to a positioning device for use with a medical device to assist a user in maintaining the medical device in a desired 3-dimensional orientation, comprising: an anchor for releasably attaching the medical device to the positioning device; a laser for generating an indication of orientation on a surface; an accelerometer for providing an indication of orientation relative to gravity; and a display for providing an indication of said orientation to the user to inform the user to adjust a position of the device relative to the desired position.

A further embodiment is related to a method of performing a medical procedure comprising performing a first CT scan and determining a trajectory and entry point for a medical device; utilizing a first laser line from a CT scanner and aligning the first laser line with a second laser line attached to a guidance apparatus; wherein the trajectory of the predetermined path can be maintained by maintaining the alignment between the first laser line and the second laser line along the predetermined path angle as determined by an accelerometer.

A further embodiment is directed to a positioning device for use with a medical device to assist a user in maintaining the medical device in a desired 3-dimensional orientation, comprising: an anchor for releasably attaching the medical device to the positioning device; a laser for generating an indication of orientation on a surface; an accelerometer for providing an indication of orientation relative to gravity in the axial and craniocaudal planes; and a display for providing an indication of said orientation to the user to inform the user to adjust a position of the device relative to the desired position; wherein said anchor comprises a clip and a rubber grommet having at least one opening suitable for insertion of a medical device, and wherein said clip secures around said rubber grommet, thereby securing the medical device to said positioning device.

A further embodiment is directed to a method of performing a surgical procedure comprising: performing a CT scan on a patient; determining a surgical plan comprising a point of entry and a predetermined trajectory; displaying a first laser line from a CT scanner on the patient; utilizing a guided medical apparatus, comprising a housing comprising a display, an accelerometer, a laser displaying a second laser line, and an attached medical device; wherein the medical device is positioned along the predetermined trajectory by aligning the first laser line with the second laser line to orient the medical device along a first plane; wherein once aligned in the first plane, the accelerometer data is utilized to align the medical device along the predetermined trajectory; and advancing the medical device along the predetermined trajectory to perform the surgical procedure.

Additional features and embodiments will be apparent to one of ordinary skill in the art upon consideration of the following detailed description of preferred embodiments and descriptions of the best mode of carrying out the invention.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "CT" or "CT guidance" refers to any and all methods of providing a 2D or 3D image data for medical procedures including, but not limited to, computed tomography (CT), magnetic resonance imaging (MRI), ultrasound, fluoroscopy, or other medical imaging modalities that produce dimensional image data.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The present invention is related to a positioning apparatus that provides real-time feedback to a user to assist with positioning a medical device within a specific location in a body, and methods for using said positioning apparatus. In the most general sense, the invention includes a device for holding a surgical instrument that includes a laser line generator and an orienting component. The laser line generator displays a visual laser line that is aligned with a displayed CT laser line and the orienting component ensures the device is positioned at the desired angulation. In this manner, the device can be suitably used with surgical tools wherein the device can grasp the surgical tool, and then the visual laser line is aligned with a displayed CT laser line to orient the device to the axis of the CT scanner and wherein the orienting component ensures that the device is oriented with the correct angulation of the planned trajectory, without the need to re-scan the patient to determine position of the device. Compared to the prior art, the invention is able to reduce the number of CT scans needed to place a surgical instrument at a specific place in the body.

Figure 1:
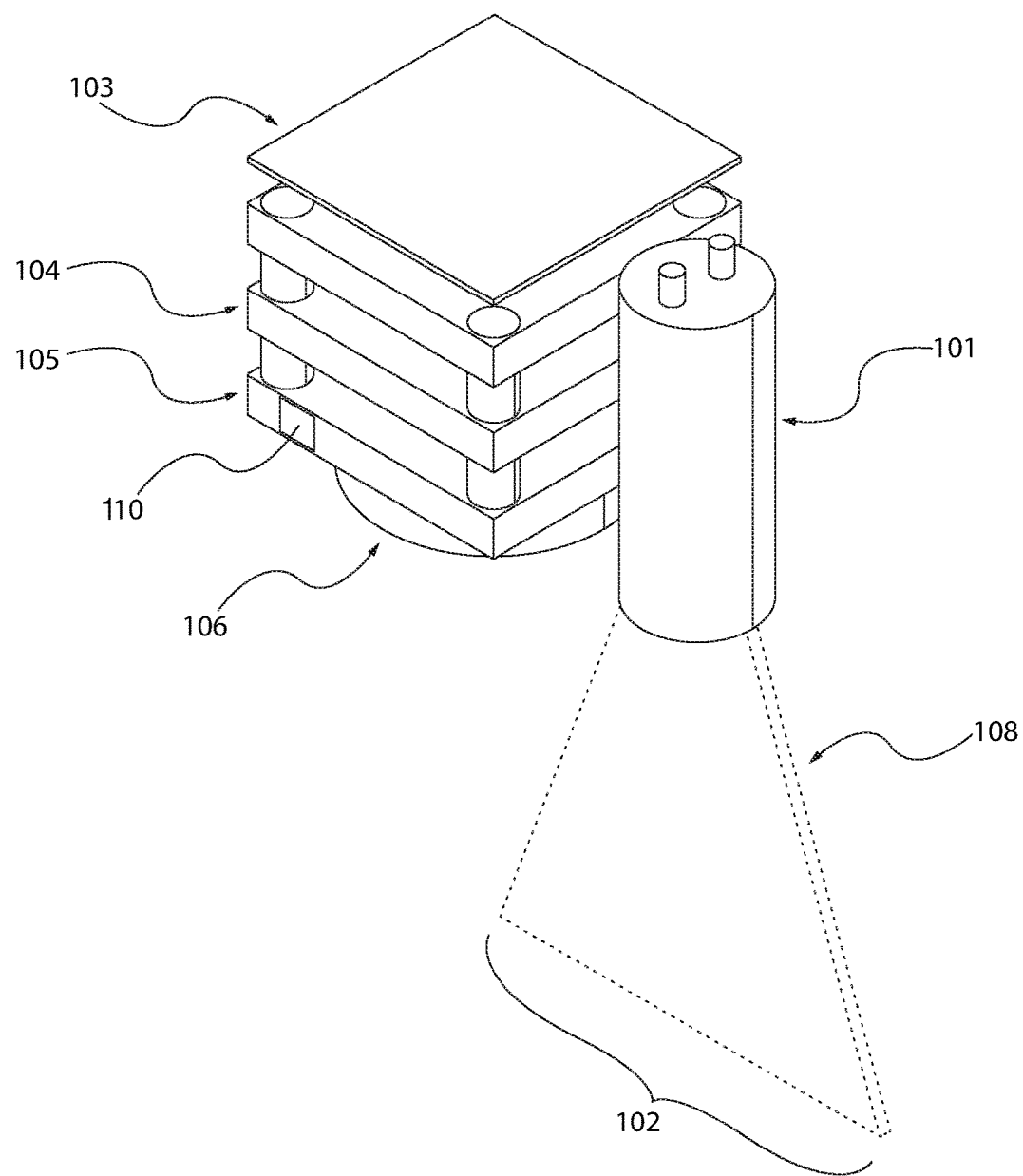
FIG. 1 provides a depiction of an embodiment of a laser and accelerometer guided apparatus.

An embodiment of the device is depicted in FIG. 1. As depicted in FIG. 1, the device consists of a line-generating laser 101, an electronic force measurement device such as an accelerometer 104, a microcontroller 105, a display 103 such as an LCD or OLED, an on/off switch 110, and a battery 106. The accelerometer 104, microcontroller 105, display 103, on/off switch 110, and battery 106 are components known to one of ordinary skill in the art as utilized for medical devices and other small electronic devices. The exact components are interchangeable with the numerous suitable components based on the size, accuracy, display etc., suitable for the particular device.

Figure 2A:
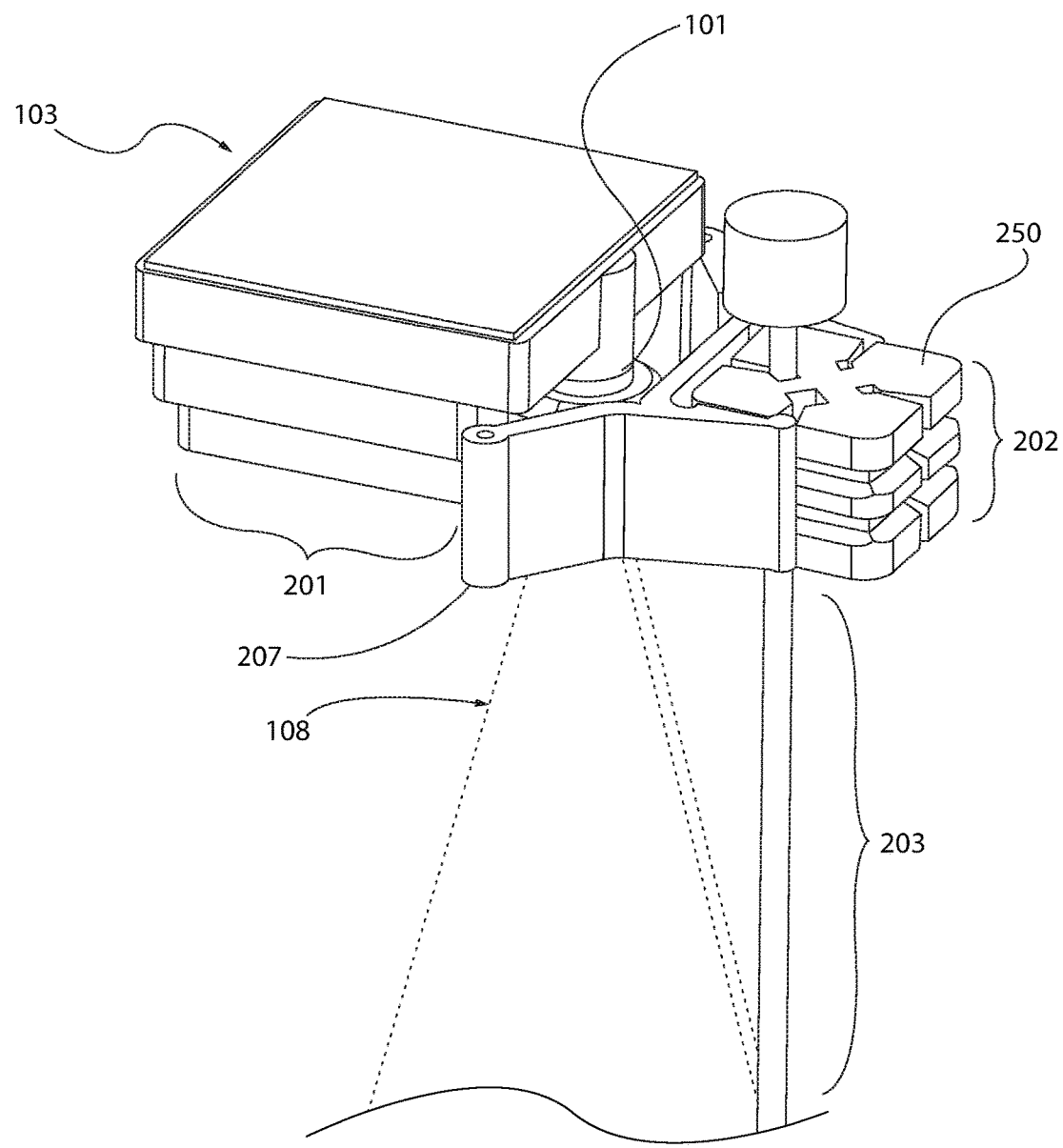
FIGS. 2A and 2B depict an embodiment of a laser and accelerometer guided apparatus attached to a medical instrument and a perspective view of a grasping component of one embodiment.
Figure 2B:
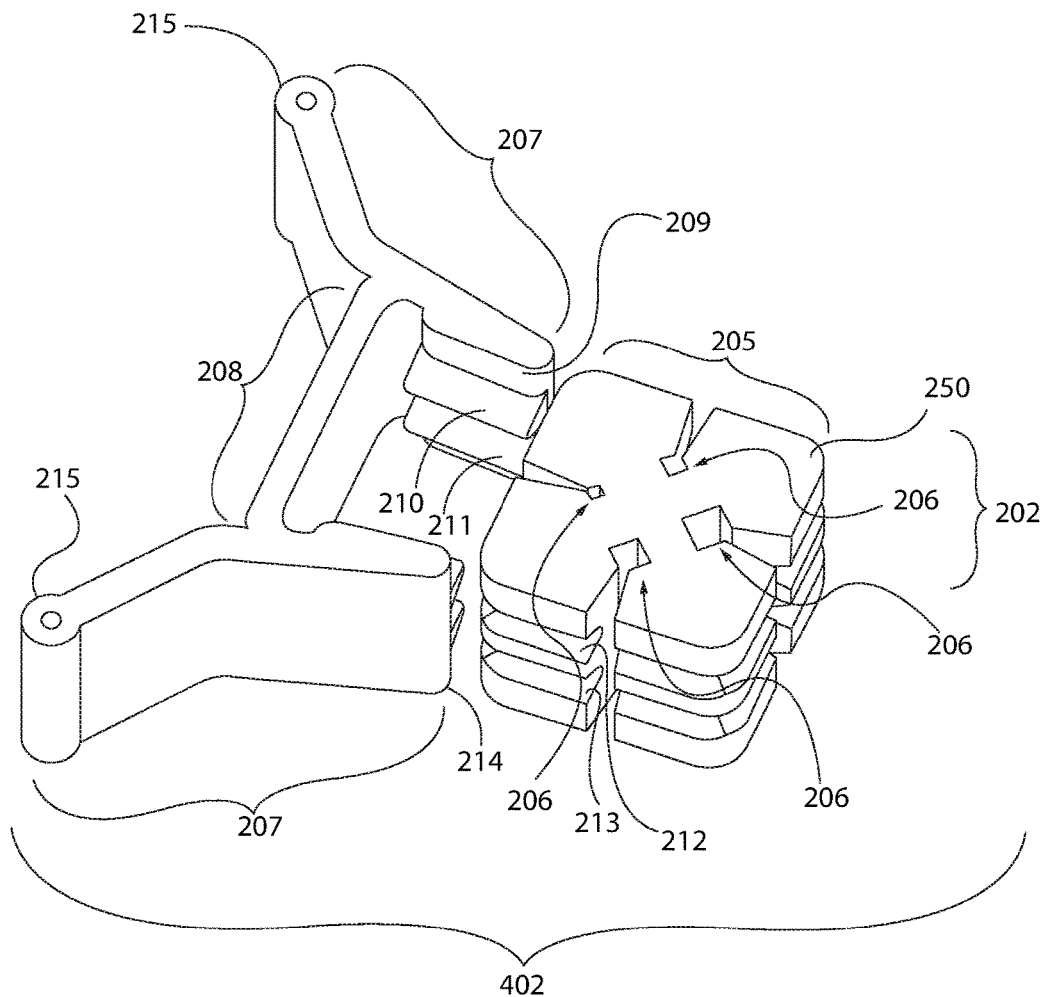

Further depicted in FIG. 2 is a housing unit 201 (FIG. 2A), and an anchor 402 (FIG. 2B), which refers to the components that attach a medical instrument 203 to the positioning device. As described herein, several suitable anchor devices may be utilized to connect a medical device to the positioning device. Alternatively, the positioning device is manufactured with an attached medical device in certain embodiments.

FIG. 2A identified an external housing 201, as depicted as a box shaped housing and contains the battery 106, microcontroller 105, line-generating laser 101, and accelerometer 104 within the housing. The size and shape of the external housing 201 is defined by the size of the components, and the goal is to make the housing 201 as small as reasonably possible to allow for maximum dexterity of the device, while still providing for the necessary components. The display 103 would mount onto the external housing 201. In alternative embodiments, the display 103 is contained within the external housing 201 and displayed through an aperture or transparent window in the top portion of the housing. In further embodiments, the display is remote to the device and information displayed on the display is transmitted wirelessly thereto, via a transmittal positioned within the external housing 201. As typical with ordinary electrical devices having a battery, an on/off switch 110 is utilized to power up and power down the device.

The line generating laser 101 is mounted within the housing 201 along the laser's longitudinal axis, so as to orient and project a visible laser line 108 emanating from the distal end of the laser 101, wherein the visible laser line 108 is displayed perpendicular to the long axis of the medical instrument 203. As is depicted in FIG. 1, the visible laser line 108 has a divergence of 102, and this divergence 102 is perpendicular to the longitudinal axis of the medical instrument. This visible laser line 108 results in a visible line on a surface, wherein the visible line can be superimposed onto a displayed CT scan, to provide for orientation of a first axis for the device.

FIG. 2A provides a further depiction of the device, wherein the visible laser line 108 is projected from the distal end of the laser 101, such that the visible laser line 108 extends down from the laser 101 to be parallel to a medical instrument 203. Thus, the visible laser line 108 is in the same plane as the medical instrument 203, and that plane and line can be positioned and oriented as necessary by the user, to project upon a surface as shown by divergence 102. The use of the visible laser line 108 provides a mechanism to ensure that the device, once positioned, remains aligned with the axis of the CT scanner. Thus, importantly, the visible laser line 108 enables the device to stay properly oriented, as a rotation of the device would mean that the visible laser line 108 would not be within the plane of the planned trajectory. Indeed, the laser provides one component of the correct trajectory i.e. the heading (north, south, east, west, and everything in between), whereas the accelerometer provides the angulation with respect to gravity, but provides no information on which way the device is pointing in regards to the heading. So the laser fixes the heading to the axis of the CT scanner.

Further depicted in FIG. 2A is the anchor 402 comprising a device holder 250 and clip components. As depicted, the device holder is positioned within a clip like structure, with one side of the clip 207 prominently visible. The anchor components are more prominently displayed in FIG. 2B, which depicts the two clip sides 207, as well as the clip base 208. The clip base 208 is secured to a portion of the housing 201 to secure it to the device. The sides of the clip 207 can be compressed at the wings 215 and increase the opening 214 to accept the device holder 250. The wings 215, base 208, and sides 207 that make up the clip are preferably a plastic or polymer material.

The device holder 250 is preferably made of a plastic, rubber, or polymer material, and is both flexible and elastic, as it easily returns to its original shape after use. The device holder 250 has a height 202 and a width 205 (being a square). The clip base 208 has a width of about the same as the width 205, wherein the device holder can be inserted into the opening and fit within the clip. Further defined on the device holder 250 are a first 212 and second 213 concave indentations, positioned on each of the four sides of the device holder 250. These concave indentations have corresponding convex protrusions 210 and 211 within the jaws of the clip holder. Accordingly, the wings 215 can be compressed to open the jaws of the clip holder and to accept the device holder 250 within the jaws. Upon release of pressure from the wings 215, the properties of the clip holder compress the jaws around the device holder 250 to secure it into place.

Advantageously, the device holder 250 comprises four openings 206, extending from the top to the bottom of the clip holder along the height 202 of the clip holder. These openings 206 are suitable for accepting a medical device there within. As is shown, the openings 206 are of different sizes to accommodate medical devices of different diameters. Upon contact and compression by the jaws, a device, placed within the opening 206, will be compressed and secured in place.

Figure 3A:
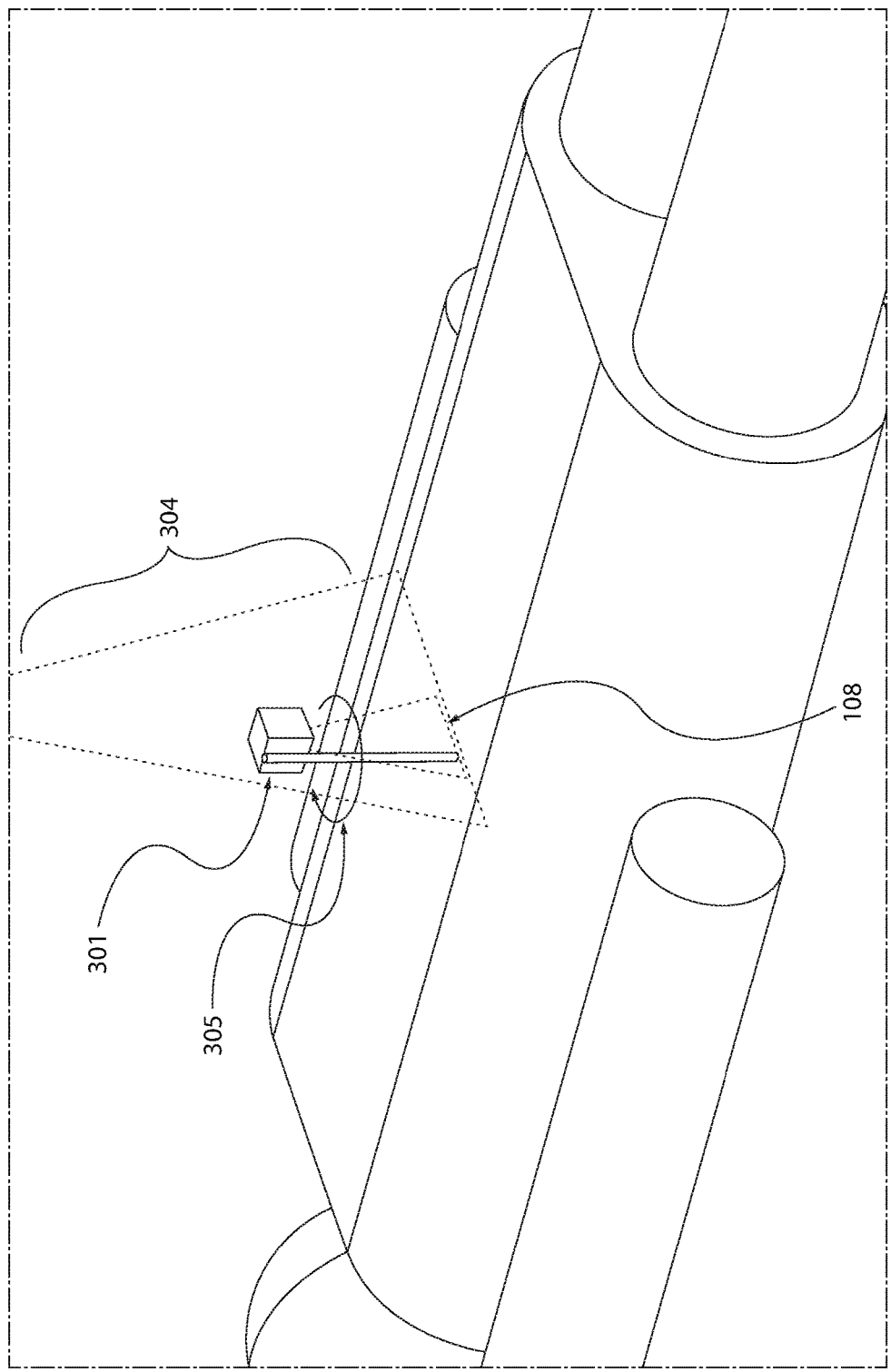
FIG. 3A depicts an embodiment of a laser and accelerometer guided apparatus attached to a medical instrument and aligned with the laser line of a CT scanner.
Figure 3B:
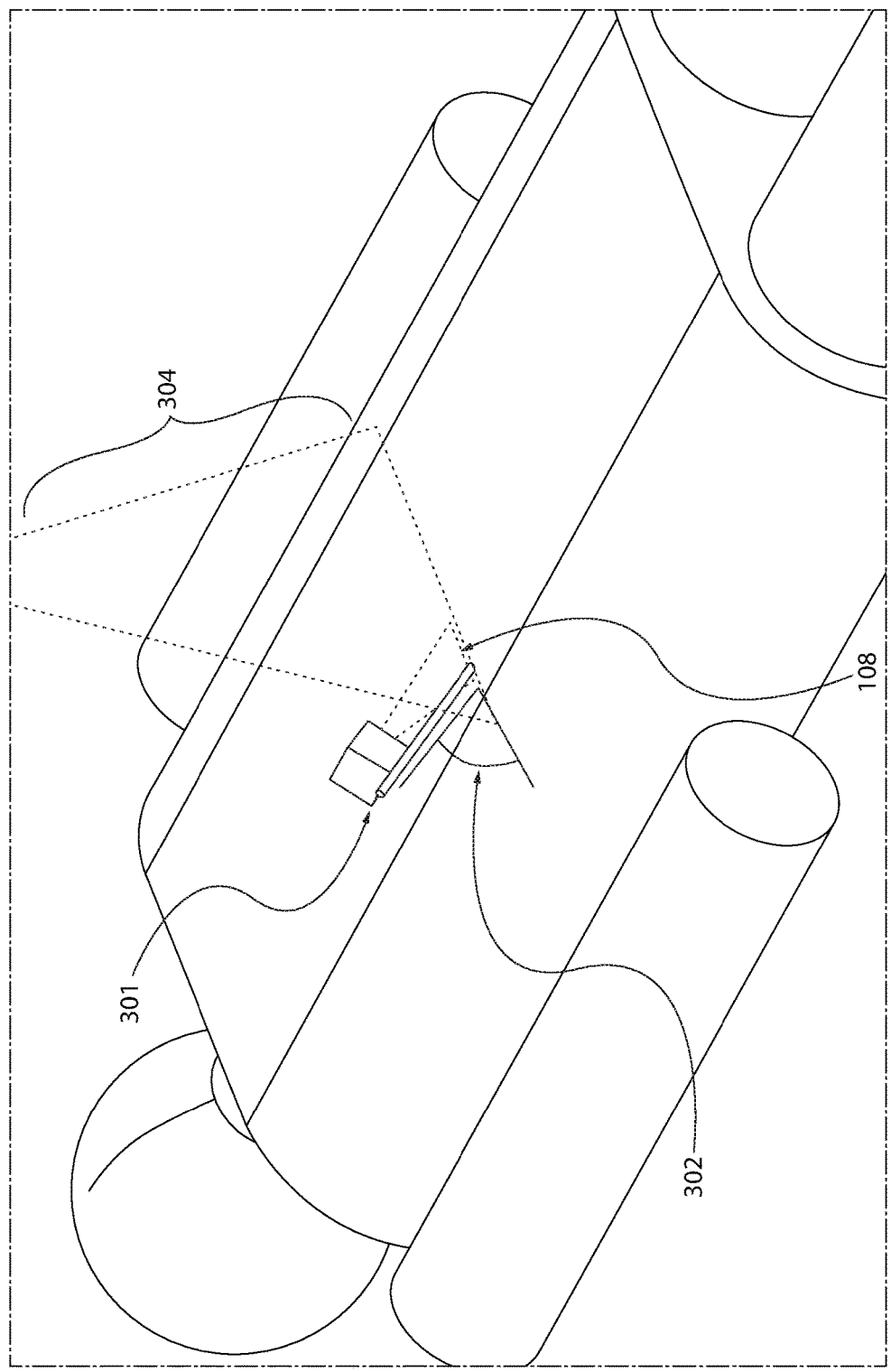
FIG. 3B depicts an embodiment of a laser and accelerometer guided apparatus attached to a medical instrument, aligned with the laser line of a CT scanner, and oriented at a tilt angle in the axial plane.
Figure 3C:
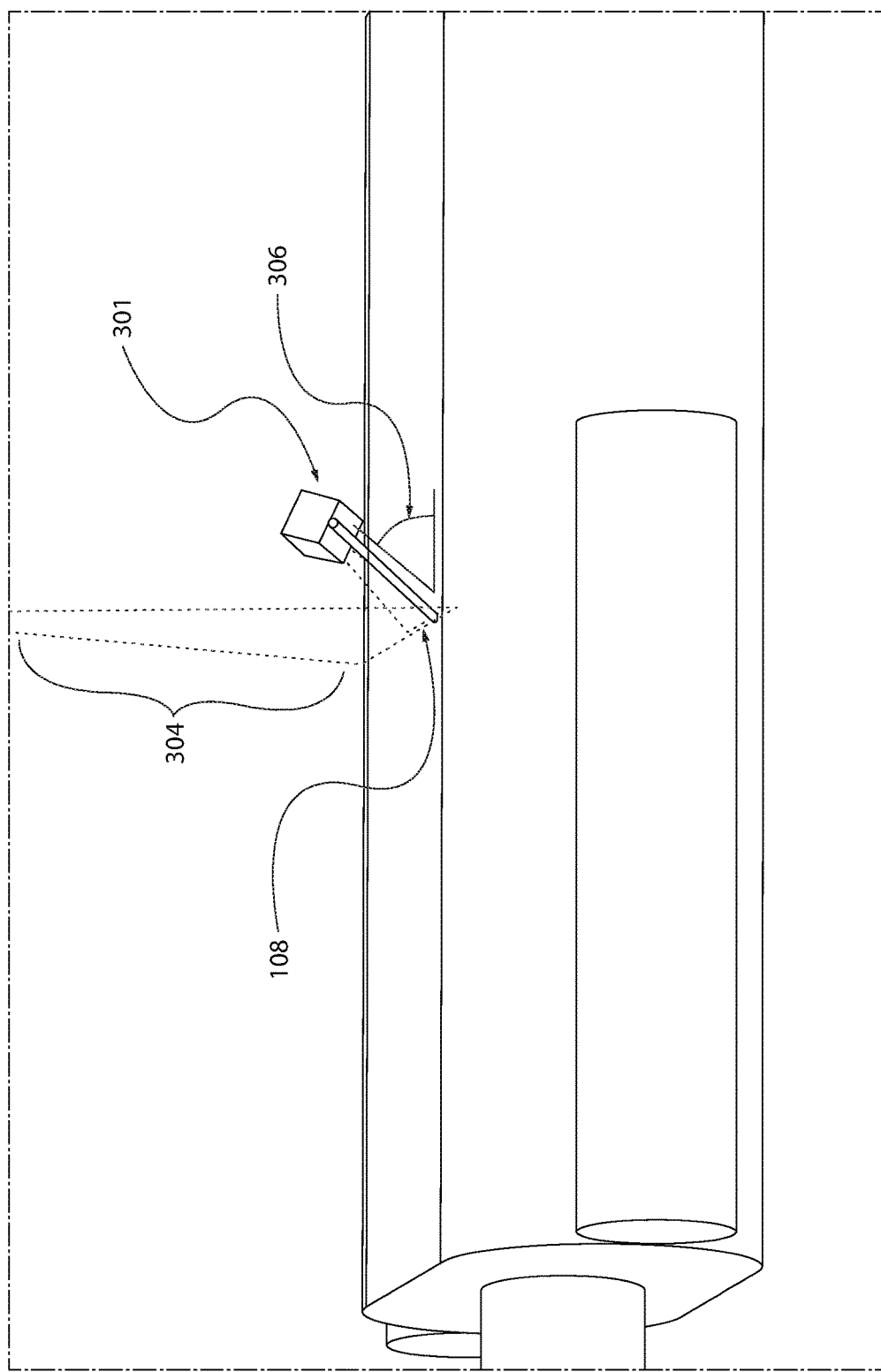
FIG. 3C depicts an embodiment of a laser and accelerometer guided apparatus attached to a medical instrument, aligned with the laser line of a CT scanner, and oriented at tilt angle with components in the axial plane and craniocaudal direction.

As depicted in FIGS. 3A-3C, the visible laser line 108 generated by the device 301 can be aligned with a laser line generated by a CT scanner 304. By keeping the two laser lines superimposed, two things are accomplished. First, the device and attached medical instrument are aligned with the axis of the CT scanner, and second, rotation around an axis parallel to gravity 305, which is not detected by the accelerometer, is prevented. With this type of rotation prevented, the orientation of the device and attached medical instrument are then only dependent upon the tilt angles 302 and 306 (shown in FIGS. 3B and 3C) with respect to gravity as determined by the accelerometer.

Indeed, the purpose of the accelerometer 104 is to allow the operator to place the device 301 with the desired tilt angles 302 and 306 as determined from the CT images at the start of the procedure. Accordingly, the data from the accelerometer 104 is processed by the microcontroller 105 into tilt angles in relation to gravity and displayed on the device display 103.

In combination, the laser line 108 and the data from the accelerometer provide 3-dimensional orientation of the device and the attached medical instrument as the medical instrument is fixed in relation to the accelerometer and the laser line 108. Any orientation in 3-dimensional space can be described by three rotation angles around a fixed Cartesian coordinate system. Rotation angles around axes perpendicular to gravity referred to as tilt angles in this document can be determined from the accelerometer. Rotation around an axis parallel to gravity does not produce a change in gravitational force on the accelerometer and thus is not detected by the accelerometer. The purpose of the laser line 108 is to keep the rotation angle around this axis constant. As stated above, when the laser line of the device is aligned with the laser line of the CT scanner the angle of rotation around an axis parallel to gravity is kept constant and aligned with the axis of the CT scanner. The orientation of the device in other dimensions is then given by rotation angles around the axes perpendicular to gravity which are determined by the accelerometer.

One common example procedure in which this device may be used would be a CT-guided biopsy of a hepatic lesion. An initial CT scan through the area of interest would be performed to determine an appropriate trajectory of the biopsy needle from the skin entry point to the target lesion. The angulation of the trajectory with respect to gravity can be easily determined with simple mathematics. This trajectory is described as two angles with respect to gravity and the patient; one angle in the axial plane (left or right) 302 and one angle in the cranial or caudal direction 306. As depicted in FIG. 3A, the device is positioned at the skin entry point and the laser line of the device 303 is aligned with the laser line of the CT scanner 304. While maintaining visual alignment of the laser lines to prevent inadvertent rotation around an axis parallel to gravity 306 as described above, the device is tilted into the desired trajectory as depicted in FIGS. 3B and 3C, wherein the device can be inserted into the patient to perform the necessary procedure.

The angles calculated by the accelerometer 104 are more easily identified by FIGS. 3B and 3C. For example, FIG. 3B depicts the device with a tilt angle only in the axial plane 302 and FIG. 3C depicts the device with a tilt angle component in the craniocaudal direction 306. As the device is tilted in this manner, the numerical and graphical representations of the tilt angles with respect to gravity are depicted on the display 103 and updated many times per second to achieve real time feedback to the operator. Once the operator has oriented the device with the attached biopsy needle along the desired trajectory, the biopsy needle is advanced into the patient and the procedure is performed in a manner familiar to those skilled in the art.

An advantage to this system is that the operator has real time feedback with complete understanding and unconstrained control of the 3-dimensional orientation of the device, e.g. a biopsy needle. Having unconstrained control over the orientation of the device is one differentiating advantage over some prior art as was discussed previously. Two additional benefits and advantages include: first, reduced radiation due to the fact the number of scans performed to obtain the desired orientation of the device are minimized, and second, that the medical instrument, e.g. the biopsy needle, maintains a singular track through the patient along a desired course and thus minimizes risk of injury to organs outside of the intended track. Of course, the reduction in number of scans required to successfully perform a procedure further ensures that the procedure is faster than prior procedures which provides additional benefits. This includes reduced doses of and time under moderate sedation or general anesthesia decreasing risk of anesthesia or sedative medication related complications, reduced costs to the hospital and physician as patient throughput would be increased, and reduced fatigue on medical professionals.

The anchor mechanism to attach the medical instrument 203 to the apparatus is mounted on the external housing 201. In other embodiments, the anchor is within the house, or the anchor is attached to the bubble housing. All components of the device are thus attached to the medical instrument as a unit and would not require any auxiliary equipment or setup. Therefore, unlike many devices, the device described herein is completely mobile within an operating room or other room where the device would be used, and the operator is not constrained with wires or other tethers to the device that would limit the mobility of the device or hinder its performance.

In certain preferred embodiments, the measurements from the accelerometer may be wirelessly transmitted to an external receiver which can then comprises a display. Alternatively, or in combination, the device may comprise visual or tone/sound generating mechanism to aid in recognition of when the device has strayed from one of the predetermined angles, and assist the operator of the device in correcting the orientation in an audible manner. For example, the display may comprise color changing indicators to identify proper orientation, slightly askew, or problematic, for example using red, yellow, and red lights to correspond to each state. Similarly, an audible sound or tone may include two or more tones to indicate proper orientation, or improper orientation. Visual stimuli may also include flashing lights, that increase or decrease in rate of flashing based on orientation. Similarly, the audible tones may increase in volume or reduce the duration between tones to indicate proper or improper orientation. Indeed, certain embodiments provide a method wherein proper alignment maintains the rate of percussion of a tone, and wherein an increasing rate of percussion signals drift from the proper trajectory path. Further embodiments flash lights at increasing rates, or modify the color or sound based on drift from the proper alignment. Similar features are present, for example in car parking sensors, targeting devices, and the like.

Figure 4A:
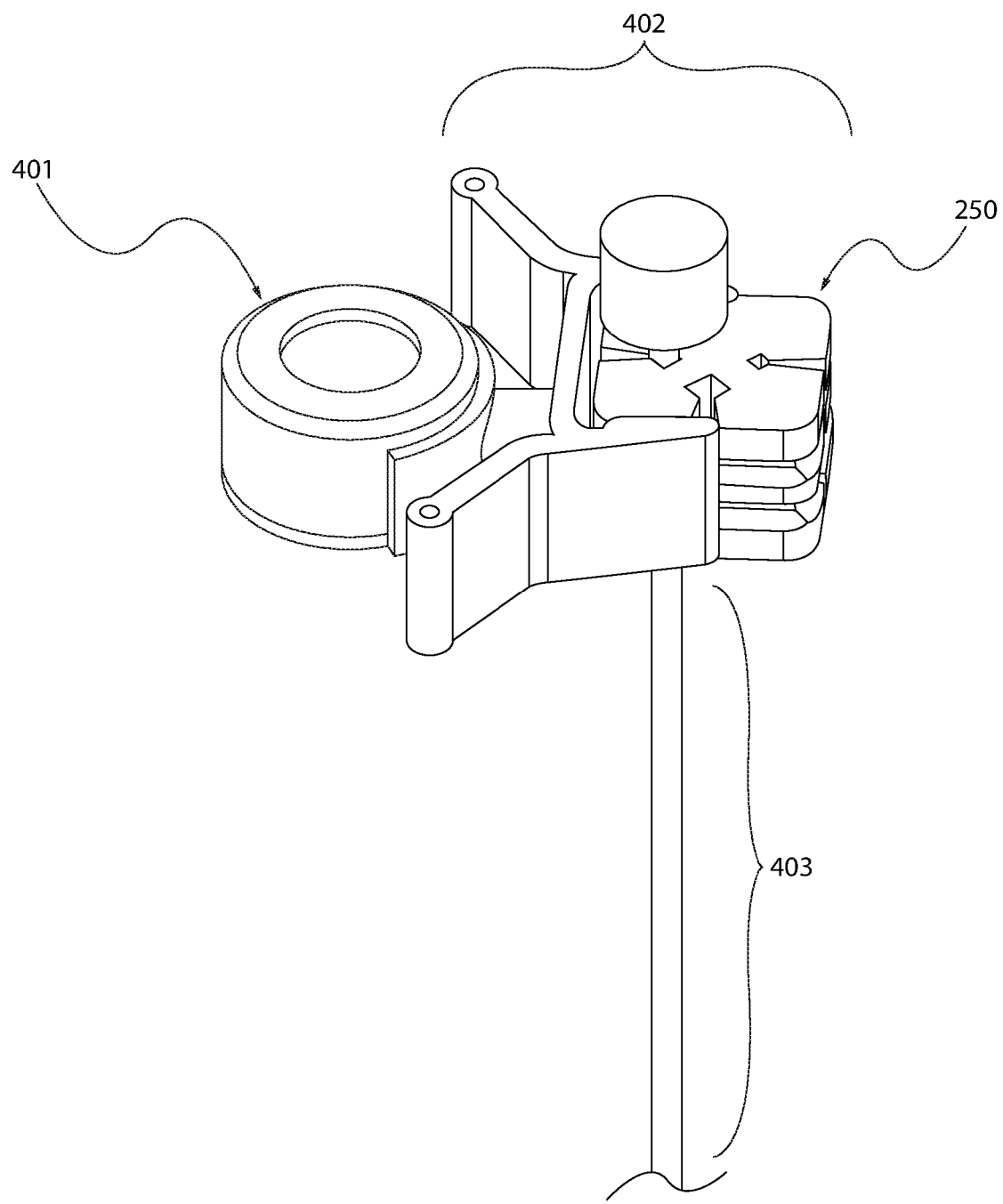
FIGS. 4A and 4B depicts an alternative embodiment consisting of a bubble level guided apparatus attached to a medical instrument.
Figure 4B:
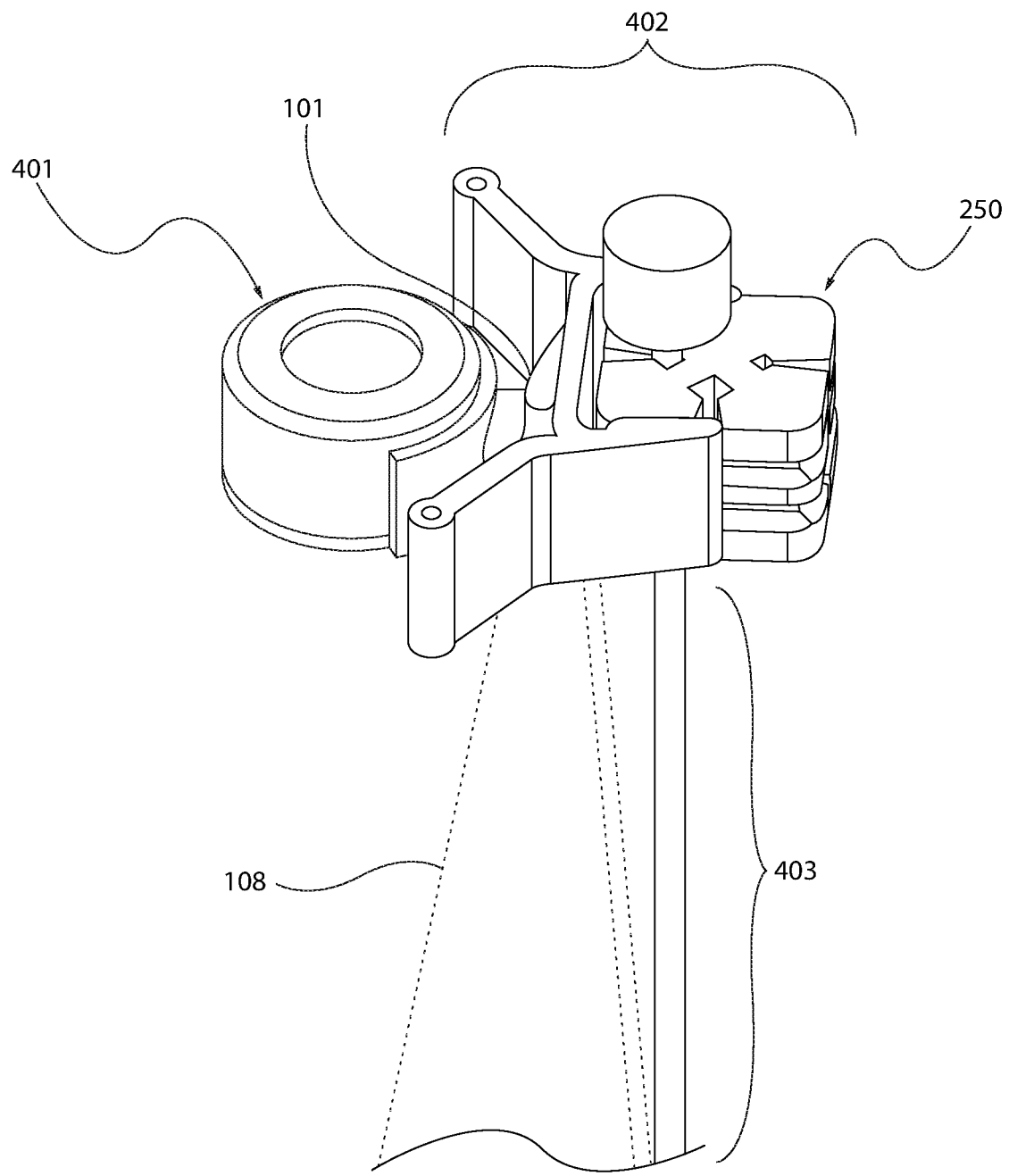

In a further embodiment, the accelerometer may be replaced by a bubble level, as depicted in FIGS. 4A and 4B. Like the accelerometer, the bubble level can provide information regarding the tilt angle of the device relative to gravity by deflection of the bubble by a distance proportional to the tilt angle.

In certain embodiments the bubble level is attached via a gyroscoping support 410 that allows the bubble level to be oriented after the position of the device is determined. In this case, after the angulation is determined in the axial plane and craniocaudal plane, the bubble level can be oriented to provide for a level orientation of the bubble level on the device itself. Thus, when the practitioner is using the device, maintaining a "level" orientation of the modified bubble level will maintain the correct axial and craniocaudal planes. In combination with an attached laser, the device can therefore accurately position the device according to the predetermined insertion path.

Furthermore, an alternative embodiment utilizes a bubble level for the sole purpose of aligning the device parallel to gravity for procedures in which no angulation with respect to gravity is desired. In this scenario, the device would also not require a line generating laser or battery and would only consist of a bubble level 401 and an anchor 402 to a medical device 403 as depicted in FIG. 4A.

Figure 5:
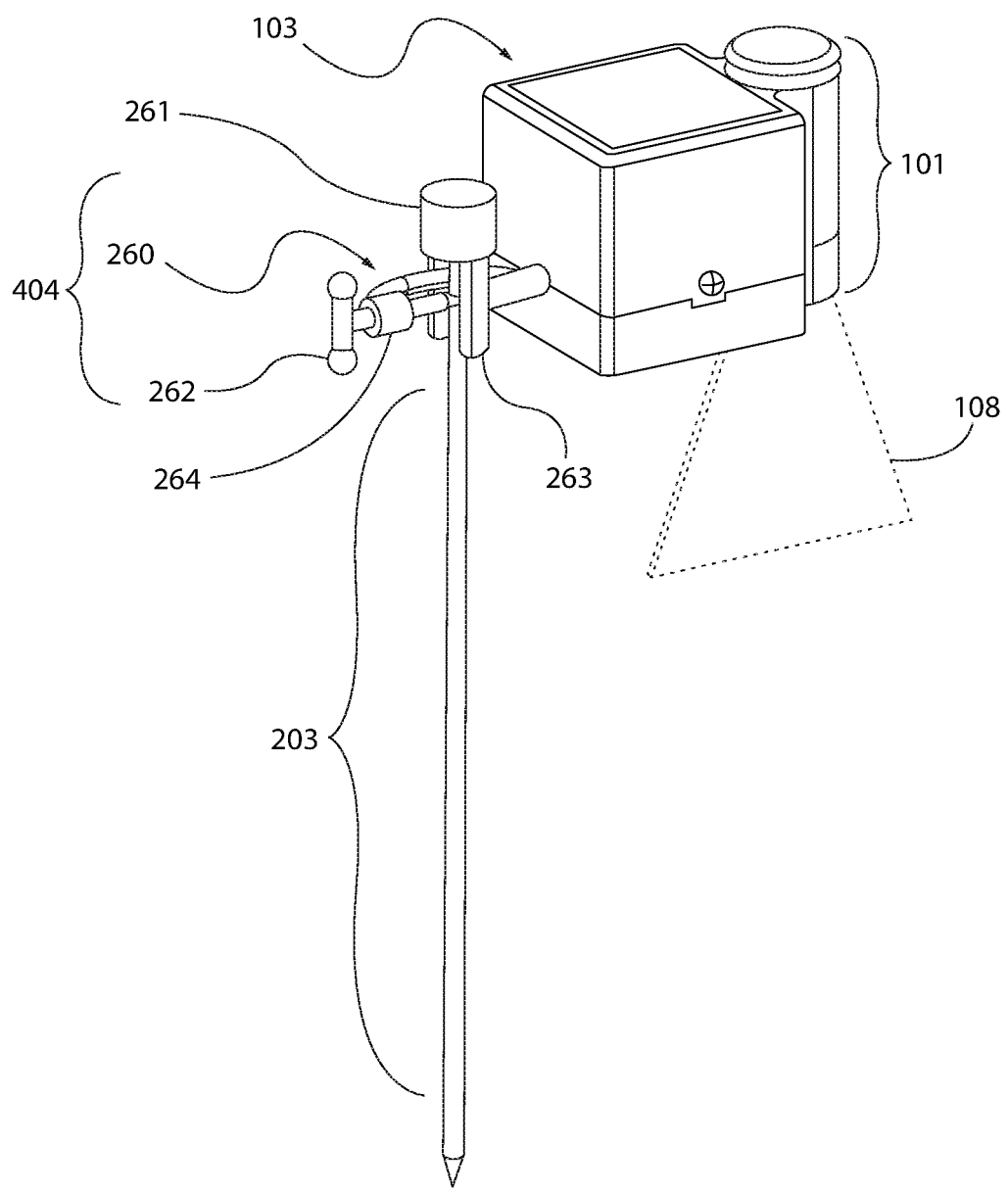
FIG. 5 depicts an embodiment of a laser and accelerometer guided apparatus and attached instrument.
Figure 6:
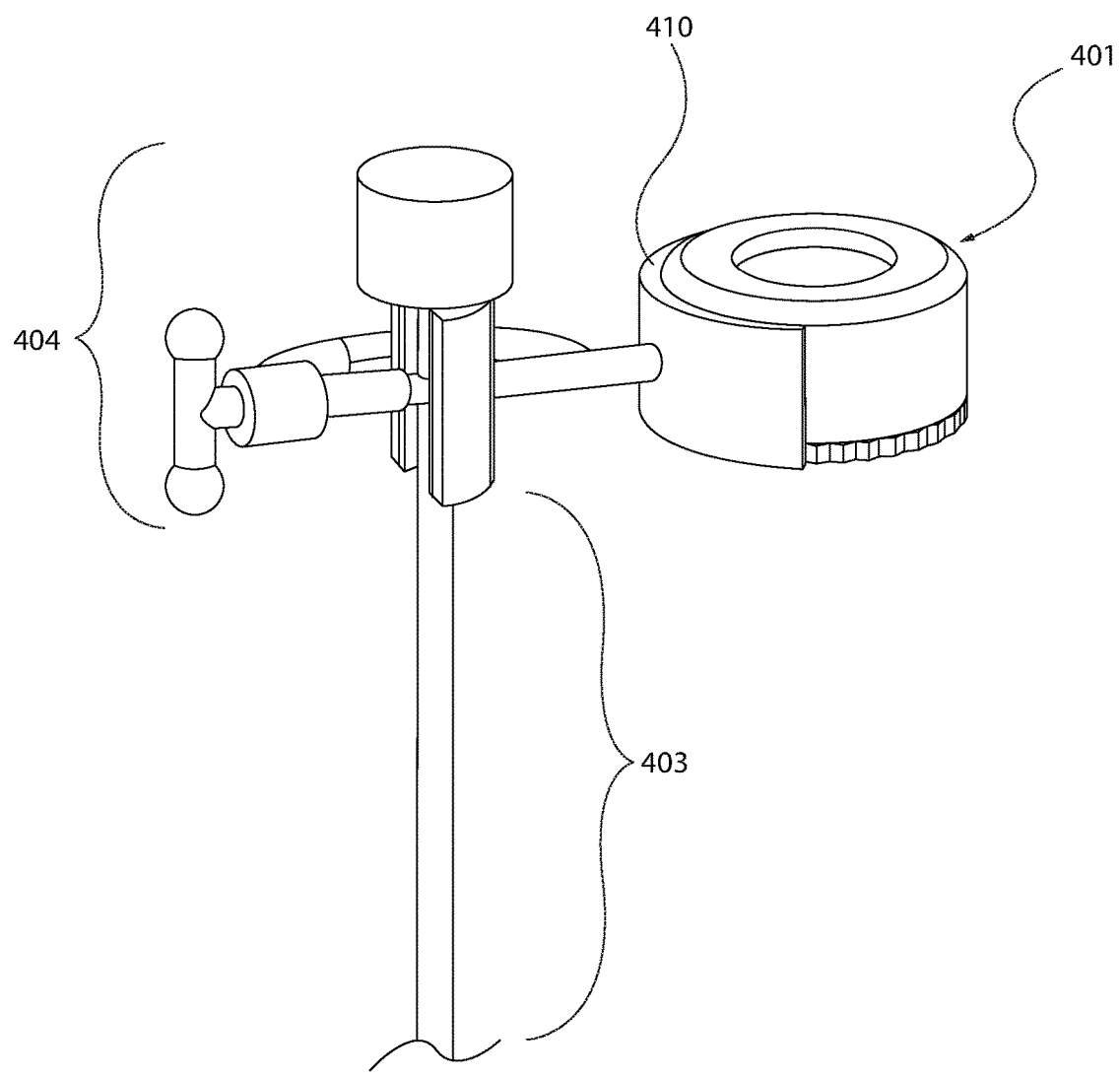
FIG. 6 depicts an embodiment of a bubble level guide.

In an alternative embodiment, the anchor mechanism is a simple vise-type mechanism with a metal half-cylinder 261 and a half-circle arm 263 with a screw hole at its apex, as provided in FIG. 5. This type of clamping device provides that the medical instrument 203 would fit in between the half-cylinder and the arm and a screw would then fit through the hole in the arm and pin the medical instrument against the metal half-cylinder. A rubber lining could be applied to the metal half-cylinder for added stability.

A further embodiment for anchoring a medical instrument to the device utilizes a compression fitting attached to the device, wherein the medical instrument includes a component on the proximal end of the instrument that is capable of fitting with a compression fitting, and be secured into place. Further examples may utilize a male/female pair attachment, with one half of the pair secured onto the device at manufacture, and the other half of the pair attached to the medical instrument. This part attached to the medical instrument may be manufactured on the medical instrument, or combined with, for example, a compression fitting or clamp, or other means to secure the matching pair of the male/female pair to the medical instrument.

However, in additional embodiments, additional anchor mechanisms as known to one of ordinary skill in the art are contemplated for use with the guidance apparatus. Any number of clamping, latching, screwing, adhering or other securing mechanisms or means is suitable to attach a medical instrument to the positioning device. However, it is necessary that the anchor mechanism provides for a secure and stable attachment to allow for precise movements and stability of the medical instrument.

It should also be known to one of ordinary skill in the art that the guidance apparatus may be an integrated component of a medical instrument in which the operator does not manually attach or remove the guidance apparatus to a medical instrument. The guidance apparatus is instead incorporated into the combined medical instrument during the manufacturing or assembly process. The mechanisms or means of integrating the guidance apparatus with a medical instrument can include, but is not limited to any of the above mentioned mechanisms or means of attachment, and further include welds, adhesives, or manufactured as a single component.

Accordingly, in a preferred embodiment, a guidance apparatus comprises an enclosure, a display, a laser, an accelerometer, a microcontroller to process the accelerometer data, a battery, and an anchor apparatus. Wherein the guidance apparatus provides a laser that is disposed on the target, in a line, perpendicular to the long axis of the medical instrument, and wherein the accelerometer enables an operator to orientate the medical instrument in the axial plane and in the craniocaudal plane to perform the necessary medical procedure.

Furthermore, the guidance apparatus provides for new methods for performing certain medical procedures. In one embodiment a method comprises performing a first CT scan to determine a plan for performing a medical procedure and determining a point of entry into the patient. The CT scan then provides a laser guidance line perpendicular to the patient. Once the plan and point of entry are determined, the guidance apparatus can be tilted to match the predetermined angle for the medical device, wherein the angle is determined from the accelerometer that provides 3-dimensional orientation. Furthermore, the attached laser line can be aligned with the CT laser line which maintains the orientation of the guidance apparatus to ensure that the accelerometer provides accurate angle information to the operator, and thereafter performing the procedure along the predetermined path by maintaining the predetermined angles according to the guidance apparatus.

Accordingly, the method allows an operator to perform a medical procedure requiring precise placement of a medical instrument along a pre-determined trajectory by aligning a line generating laser connected to a medical instrument with the laser line of a CT scanner, wherein the angle of orientation along the pre-determined path is maintained by utilizing data from the accelerometer, which is providing 3-dimensional orientation of the guidance apparatus.

Therefore, a preferred method comprises first CT scan, determining a surgical plan for a medical device; orienting the medical device to match the angle of the predetermined surgical plan by utilizing data from an accelerometer attached to the medical device; and performing the medical procedure according to the surgical plan by maintaining the medical device along the predetermined trajectory.

Having now fully described this invention, it will be understood to those of ordinary skill in the art that the device and components utilized therein, and the methods of the present invention can be carried out with a wide and equivalent range of conditions, orientations, and variations of the components and other parameters without departing from the scope of the invention or any embodiments thereof.

What is claimed is:

1. A positioning device for use with a medical device to assist provide feedback to a user indicative of a desired 3-dimensional orientation of the medical device, comprising:
   an anchor for releasably attaching the medical device to the positioning device;
   a laser for generating an indication of orientation on a surface of a patient;
   an accelerometer for providing an indication of orientation of the medical device relative to gravity by determining tilt angles in a first plane and a second plane wherein the first plane is the axial plane of the patient and the second plane is the craniocaudal plane of the patient; and
   a display for providing an indication of said orientation to the user to inform the user to adjust a position of the device relative to the desired position.

2. The positioning device of claim 1, wherein the desired position is determined by a CT scan.

3. The position device of claim 1, wherein the medical device is a biopsy needle.

4. The positioning device of claim 1, where the laser displays a line on a surface and wherein the laser is superimposed over a line from a CT scanner, and wherein by maintaining the laser line over a line from the CT scanner, the positioning device remains oriented along one axis.

5. The positing device of claim 1 further comprising a tone generating component to provide a further indication of the orientation relative to gravity.

6. The positioning device of claim 1, wherein the anchor comprises a clip and a rubber device holder suitable for compression within said clip.

7. The positioning device of claim 1, further comprising a wireless transmitter, wherein the wireless transmitter transmits data to an external receiver and display.

8. A method of performing a surgical procedure comprising:
   a. performing a CT scan on a patient;
   b. determining a surgical, plan comprising a point of entry and a predetermined trajectory;
   c. displaying a first laser line from a CT scanner on the patient;
   d. utilizing a guided medical apparatus, comprising a housing comprising a display, an accelerometer, a laser displaying a second laser line, and an attached medical device;
   e. wherein the medical device is positioned along the predetermined trajectory by aligning the first laser line with the second laser line to orient the medical device along a first plane; wherein once aligned in the first plane, the accelerometer data is utilized to align the medical device along the predetermined trajectory by determining tilt, angles in a first plane and a second plane wherein the first plane is the axial plane of the patient and the second plane is the craniocaudal plane of the patient; and f. advancing the medical device along the predetermined trajectory to perform the surgical procedure.

9. The method of claim 8, wherein the medical device is a biopsy needle.

10. The method of claim 8, further comprising a tone generating component, wherein said tone generating component provides a tone indication of the orientation relative to gravity.

11. The method of claim 8, wherein the accelerometer data provides for a visual or audible indication of whether the medical device is positioned along the predetermined trajectory.

12. The method of claim 11, wherein an indication of a proper trajectory path is indicated by a green light, and an indication of an improper trajectory path is indicated by a red light.

13. The method of claim 11, wherein an indication of a proper trajectory path is indicated by a first tone, and an indication of an improper trajectory path is indicated by a second tone.

14. The method of claim 11, wherein an indication of a proper trajectory path is indicated by a tone, wherein proper alignment of said tone maintains the rate of percussion of said tone, and wherein an increasing rate of percussion signals drift from the proper trajectory path.

15. The method of claim 8, wherein the attached medical device is secured to the guided medical apparatus via an anchor.

16. The method of claim 12, wherein said anchor comprises a clip and a rubber device holder suitable for compression within said clip.

17. A positioning device for use with a medical device to provide feedback to a user indicative of a desired 3-dimensional orientation of the medical device, comprising:
an anchor for releasably attaching the medical device to the positioning device;
a laser for generating an indication of orientation on a surface;
an accelerometer for providing an indication of orientation of the medical device relative to gravity via tilt angles in the axial and craniocaudal planes; and
a display for providing an indication of said orientation to the user to inform the user to adjust a position of the device relative to the desired position;
wherein said anchor comprises a clip and a rubber grommet having at least one opening suitable for insertion of a medical, device, and wherein said clip secures around said rubber grommet, thereby securing the medical device to said positioning device.

* * * * *